(12) United States Patent
Eggen et al.

(10) Patent No.: US 12,194,292 B2
(45) Date of Patent: *Jan. 14, 2025

(54) INTERVENTIONAL MEDICAL DEVICE AND METHOD OF USE

(71) Applicant: Medtronic, Inc., Minneapolis, MN (US)

(72) Inventors: Michael D. Eggen, Chisago City, MN (US); James K. Carney, Roseville, MN (US); Matthew D. Bonner, Plymouth, MN (US); Vladimir Grubac, Brooklyn Park, MN (US); Douglas S. Hine, Forest Lake, MN (US); Thomas D. Brostrom, Wayzata, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,993

(22) Filed: May 5, 2023

(65) Prior Publication Data

US 2023/0270999 A1 Aug. 31, 2023

Related U.S. Application Data

(63) Continuation of application No. 16/686,617, filed on Nov. 18, 2019, now Pat. No. 11,684,775, which is a
(Continued)

(51) Int. Cl.
*A61N 1/05* (2006.01)
*A61N 1/375* (2006.01)

(52) U.S. Cl.
CPC ......... *A61N 1/057* (2013.01); *A61N 1/37518* (2017.08); *A61N 1/3756* (2013.01)

(58) Field of Classification Search
CPC ... A61N 1/057; A61N 1/37518; A61N 1/3756
See application file for complete search history.

(56) References Cited

U.S. PATENT DOCUMENTS

| 376,207 A | 1/1888 | Pavlik |
| 3,814,104 A | 6/1974 | Irnich et al. |

(Continued)

FOREIGN PATENT DOCUMENTS

| EP | 1365702 A1 | 12/2003 |
| EP | 1670360 A2 | 6/2006 |

(Continued)

OTHER PUBLICATIONS (PCT/US2014/057596) PCT Notification of Transmittal of the International Search Report and the Written Opinion of the International Searching Authority, mailed Dec. 5, 2014, 12 pages.
(Continued)

*Primary Examiner* — Eugene T Wu
(74) *Attorney, Agent, or Firm* — Shumaker & Sieffert, P.A.

(57) ABSTRACT

A relatively compact implantable medical device includes a fixation member formed by a plurality of fingers mounted around a perimeter of a distal end of a housing of the device; each finger is elastically deformable from a relaxed condition to an extended condition, to accommodate delivery of the device to a target implant site, and from the relaxed condition to a compressed condition, to accommodate wedging of the fingers between opposing tissue surfaces at the target implant site, wherein the compressed fingers hold a cardiac pacing electrode of the device in intimate tissue contact for the delivery of pacing stimulation to the site. Each fixation finger is preferably configured to prevent penetration thereof within the tissue when the fingers are compressed and wedged between the opposing tissue surfaces. The pacing electrode may be mounted on a pacing
(Continued)

extension, which extends distally from the distal end of the device housing.

29 Claims, 9 Drawing Sheets

Related U.S. Application Data continuation of application No. 14/518,261, filed on Oct. 20, 2014, now Pat. No. 10,478,620.

(60) Provisional application No. 62/041,954, filed on Aug. 26, 2014.

(56) References Cited

U.S. PATENT DOCUMENTS

| | | | |
|---|---|---|---|
| 3,835,864 | A | 9/1974 | Rasor et al. |
| 3,902,501 | A | 9/1975 | Citron et al. |
| 3,939,843 | A | 2/1976 | Smyth |
| 3,943,936 | A | 3/1976 | Rasor et al. |
| 4,103,690 | A | 8/1978 | Harris |
| 4,142,530 | A | 3/1979 | Wittkampf |
| 4,269,198 | A | 5/1981 | Stokes |
| 4,280,512 | A | 7/1981 | Karr |
| 4,424,551 | A | 1/1984 | Stevenson et al. |
| 4,858,623 | A | 8/1989 | Bradshaw et al. |
| 4,936,823 | A | 6/1990 | Colvin |
| 5,184,625 | A | 2/1993 | Cottone, Jr. et al. |
| 5,193,540 | A | 3/1993 | Schulman et al. |
| 5,256,158 | A | 10/1993 | Tolkoff et al. |
| 5,411,535 | A | 5/1995 | Fujii et al. |
| 5,492,119 | A | 2/1996 | Abrams |
| 5,562,678 | A | 10/1996 | Booker |
| 5,573,540 | A | 11/1996 | Yoon |
| 5,642,736 | A | 7/1997 | Avitall |
| 5,683,447 | A | 11/1997 | Bush et al. |
| 5,836,960 | A | 11/1998 | Kolesa et al. |
| 5,868,754 | A | 2/1999 | Levine et al. |
| 5,916,214 | A | 6/1999 | Cosio et al. |
| 6,007,558 | A | 12/1999 | Ravenscroft et al. |
| 6,151,525 | A | 11/2000 | Soykan et al. |
| 6,152,144 | A | 11/2000 | Lesh et al. |
| 6,240,322 | B1 | 5/2001 | Peterfeso et al. |
| 6,286,512 | B1 | 9/2001 | Loeb et al. |
| 6,409,674 | B1 | 6/2002 | Brockway et al. |
| 6,575,967 | B1 | 6/2003 | Leveen et al. |
| 6,582,443 | B2 | 6/2003 | Cabak et al. |
| 6,716,238 | B2 | 4/2004 | Elliott |
| 6,783,499 | B2 | 8/2004 | Schwartz |
| 6,915,149 | B2 | 7/2005 | Ben-Haim |
| 6,926,669 | B1 | 8/2005 | Stewart et al. |
| 6,941,169 | B2 | 9/2005 | Pappu |
| 6,978,178 | B2 | 12/2005 | Sommer et al. |
| 7,149,587 | B2 | 12/2006 | Wardle et al. |
| 7,290,743 | B2 | 11/2007 | Nowack |
| 7,418,298 | B2 | 8/2008 | Shiroff et al. |
| 7,497,844 | B2 | 3/2009 | Spear et al. |
| 7,509,169 | B2 | 3/2009 | Eigler et al. |
| 7,515,971 | B1 | 4/2009 | Doan |
| 7,566,336 | B2 | 7/2009 | Corcoran et al. |
| 7,623,899 | B2 | 11/2009 | Worley et al. |
| 7,647,124 | B2 | 1/2010 | Williams |
| 7,729,782 | B2 | 6/2010 | Williams |
| 8,032,220 | B2 | 10/2011 | Kuzma |
| 8,353,940 | B2 | 1/2013 | Benderev |
| 8,364,280 | B2 | 1/2013 | Marnfeldt et al. |
| 8,473,023 | B2 | 6/2013 | Worley et al. |
| 8,500,733 | B2 | 8/2013 | Watson |
| 8,504,156 | B2 | 8/2013 | Bonner et al. |
| 8,606,369 | B2 | 12/2013 | Williams et al. |
| 8,615,310 | B2 | 12/2013 | Khairkhahan et al. |
| 8,634,919 | B1 | 1/2014 | Hou et al. |
| 8,795,328 | B2 | 8/2014 | Miles et al. |
| 9,119,959 | B2 | 9/2015 | Rys et al. |
| 9,155,882 | B2 | 10/2015 | Grubac et al. |
| 9,283,381 | B2 | 3/2016 | Grubac et al. |
| 9,526,522 | B2 | 12/2016 | Wood et al. |
| 9,675,798 | B2 | 6/2017 | Grubac et al. |
| 10,071,243 | B2 | 9/2018 | Kuhn et al. |
| 10,478,620 | B2 | 11/2019 | Eggen et al. |
| 11,110,278 | B2 | 9/2021 | Ward et al. |
| 11,197,996 | B2 | 12/2021 | Gardeski et al. |
| 11,207,530 | B2 | 12/2021 | Wood et al. |
| 11,583,658 | B2 | 2/2023 | Yang et al. |
| 2002/0103424 | A1 | 8/2002 | Swoyer et al. |
| 2002/0165537 | A1 | 11/2002 | Kelley et al. |
| 2002/0165589 | A1 | 11/2002 | Imran et al. |
| 2002/0183823 | A1 | 12/2002 | Pappu |
| 2002/0183824 | A1 | 12/2002 | Borgersen et al. |
| 2003/0088301 | A1 | 5/2003 | King |
| 2004/0116993 | A1 | 6/2004 | Clemens et al. |
| 2004/0133089 | A1 | 7/2004 | Kilcoyne et al. |
| 2004/0147973 | A1 | 7/2004 | Hauser |
| 2004/0215307 | A1 | 10/2004 | Michels et al. |
| 2004/0230281 | A1 | 11/2004 | Heil et al. |
| 2004/0260241 | A1 | 12/2004 | Yamamoto et al. |
| 2005/0004602 | A1 | 1/2005 | Hart et al. |
| 2005/0004641 | A1 | 1/2005 | Pappu |
| 2005/0004644 | A1 | 1/2005 | Kelsch et al. |
| 2005/0080470 | A1 | 4/2005 | Westlund et al. |
| 2005/0136385 | A1 | 6/2005 | Mann et al. |
| 2006/0084965 | A1 | 4/2006 | Young |
| 2006/0085039 | A1* | 4/2006 | Hastings ............ A61N 1/37288 607/9 |
| 2006/0085041 | A1 | 4/2006 | Hastings et al. |
| 2006/0136070 | A1 | 6/2006 | Pinchuk |
| 2006/0247753 | A1 | 11/2006 | Wenger et al. |
| 2007/0060961 | A1* | 3/2007 | Echt ................... A61N 1/36514 607/9 |
| 2007/0083230 | A1 | 4/2007 | Javois |
| 2007/0112405 | A1 | 5/2007 | Williams et al. |
| 2007/0156114 | A1 | 7/2007 | Worley et al. |
| 2007/0219590 | A1 | 9/2007 | Hastings et al. |
| 2008/0021532 | A1* | 1/2008 | Kveen ................... A61N 1/362 607/115 |
| 2008/0057100 | A1 | 3/2008 | Williams et al. |
| 2008/0097482 | A1 | 4/2008 | Bain et al. |
| 2009/0082828 | A1 | 3/2009 | Ostroff |
| 2009/0171159 | A1 | 7/2009 | Jorgensen et al. |
| 2009/0287187 | A1 | 11/2009 | Legaspi et al. |
| 2010/0094314 | A1 | 4/2010 | Hemlund et al. |
| 2010/0228279 | A1 | 9/2010 | Miles et al. |
| 2010/0274227 | A1 | 10/2010 | Khairkhahan et al. |
| 2011/0144572 | A1 | 6/2011 | Kassab et al. |
| 2011/0251660 | A1 | 10/2011 | Griswold |
| 2011/0270340 | A1 | 11/2011 | Pellegrini |
| 2012/0059448 | A1 | 3/2012 | Parker et al. |
| 2012/0172690 | A1* | 7/2012 | Anderson ............ A61N 1/0573 607/18 |
| 2012/0172892 | A1* | 7/2012 | Grubac .................. A61N 1/05 606/129 |
| 2012/0197373 | A1 | 8/2012 | Khairkhahan et al. |
| 2012/0203246 | A1 | 8/2012 | Staunton |
| 2012/0232563 | A1 | 9/2012 | Williams et al. |
| 2013/0035748 | A1 | 2/2013 | Bonner et al. |
| 2013/0079798 | A1 | 3/2013 | Tran et al. |
| 2013/0103047 | A1 | 4/2013 | Steingisser et al. |
| 2013/0131591 | A1 | 5/2013 | Berthiaume et al. |
| 2013/0131693 | A1* | 5/2013 | Berthiaume ....... A61N 1/37205 606/129 |
| 2013/0253347 | A1 | 9/2013 | Griswold et al. |
| 2013/0261726 | A1 | 10/2013 | Alger et al. |
| 2014/0039591 | A1 | 2/2014 | Drasler et al. |
| 2014/0058404 | A1 | 2/2014 | Hammack et al. |
| 2014/0180306 | A1 | 6/2014 | Grubac et al. |
| 2014/0200462 | A1 | 7/2014 | Stalker et al. |
| 2014/0207149 | A1 | 7/2014 | Hastings et al. |
| 2014/0236220 | A1 | 8/2014 | Inoue |
| 2014/0257324 | A1 | 9/2014 | Fain |
| 2015/0039070 | A1 | 2/2015 | Kuhn et al. |
| 2015/0051611 | A1 | 2/2015 | Schmidt et al. |
| 2015/0094735 | A1 | 4/2015 | Ward et al. |
| 2015/0253347 | A1 | 9/2015 | Cong et al. |

(56) References Cited

U.S. PATENT DOCUMENTS

| | | |
|---|---|---|
| 2015/0352353 A1 | 12/2015 | Rys et al. |
| 2016/0015322 A1 | 1/2016 | Anderson et al. |
| 2017/0224997 A1 | 8/2017 | Shuros et al. |
| 2017/0274202 A1 | 9/2017 | Grubac et al. |
| 2017/0354427 A1 | 12/2017 | Bonnette |
| 2018/0168503 A1 | 6/2018 | Waldhauser et al. |
| 2020/0078585 A1 | 3/2020 | Eggen et al. |
| 2022/0054829 A1 | 2/2022 | Ward et al. |

FOREIGN PATENT DOCUMENTS

| | | |
|---|---|---|
| WO | 2002022202 A2 | 3/2002 |
| WO | 02071977 A2 | 9/2002 |
| WO | 2004028348 A2 | 4/2004 |
| WO | 2005034764 A1 | 4/2005 |
| WO | 2006118865 A2 | 11/2006 |
| WO | 2013043671 A1 | 3/2013 |
| WO | 2013062793 A1 | 5/2013 |
| WO | 2015017157 A1 | 2/2015 |

OTHER PUBLICATIONS (PCT/US2015/040870) PCT Notification of Transmittal of the International Search Report and the Written Opinion of the International Searching Authority, mailed Oct. 14, 2015, 10 pages.

(PCT/US2015/043957) PCT Notification of Transmittal of the International Search Report and the Written Opinion of the International Searching Authority, mailed Nov. 11, 2015, 9 pages.

(PCT/US2014/057727) PCT Notification of Transmittal of the International Search Report and the Written Opinion of the International Searching Authority, mailed Dec. 8, 2014, 12 pages.

Dandamudi, MD, FHRS, et al., "How to perform permanent His bundle pacing in routine clinical practice," Heart Rhythm, vol. 13, No. 6, Jun. 2016, pp. 1362-1366.

Eggen et al., "Interventional Medical Systems, Devices, and Methods of Use" Chinese Patent Application No. 201580045776.8 First Office Action mailed Sep. 29, 2018, 7 pages.

Haqqani et al., "The Implantable Cardioverter-Defibrillator Lead: Principles, Progress and Promises," PACE, vol. 32, Oct. 2009, pp. 1336-1353.

International Preliminary Report on Patentability from International Application No. PCT/US2015/043957, mailed Jul. 27, 2016, 5 pp.

Prosecution History from U.S. Appl. No. 14/518,261, dated Mar. 23, 2017 through Jul. 12, 2019, 145 pp.

Prosecution History from U.S. Appl. No. 16/686,617, dated Apr. 13, 2022 through Apr. 23, 2023, 74 pp.

Response to Written Opinion mailed Nov. 11, 2015, from International Application No. PCT/US2014/010345, dated Jun. 27, 2016, 8 pp.

Stephenson, et al., "High resolution 3-Dimensional imaging of the human cardiac conduction system from microanatomy to mathematical modeling," Scientific Reports, published online Aug. 3, 2017, 13 pp.

Text Intended to Grant from counterpart European Application No. 15753548.5, dated Jul. 24, 2017, 60 pp.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

Vijayaraman, MD, FHRS, et al., "Permanent His bundle pacing: Recommendations from a Multicenter His Bundle Pacing Collaborative Working Group for standardization of definitions, implant measurements, and follow-up," Heart Rhythm, Dec. 2017, 9 pp.

Www.Wikipedia.org, "Tailhook", Feb. 2, 2015, 4 pages.

* cited by examiner

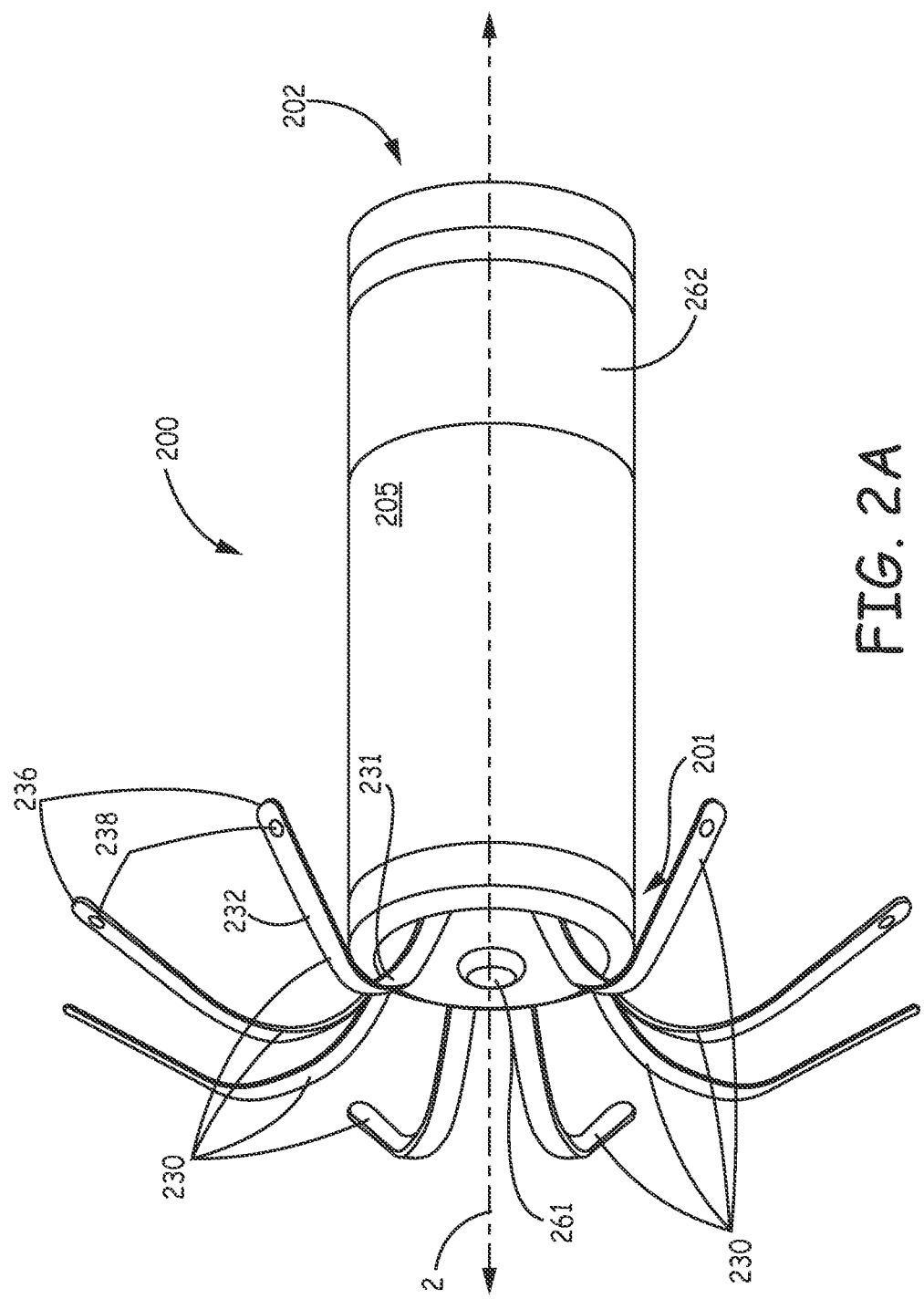

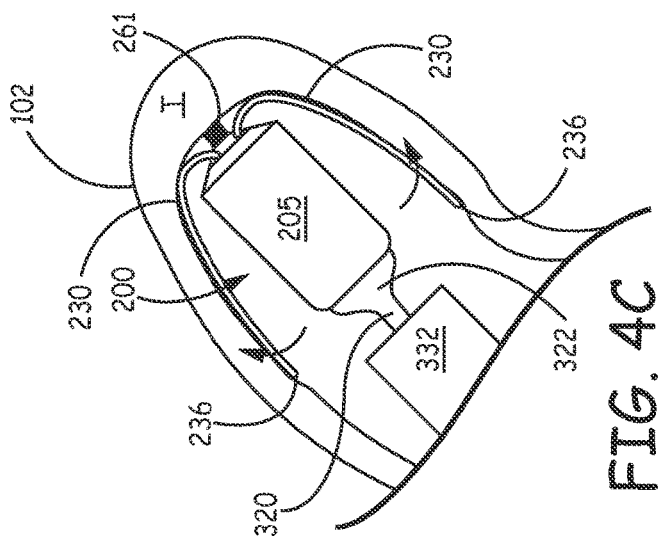
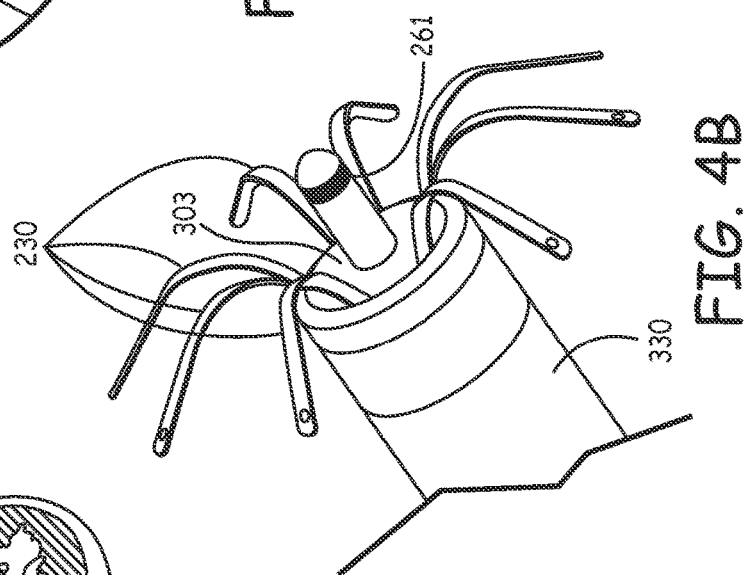
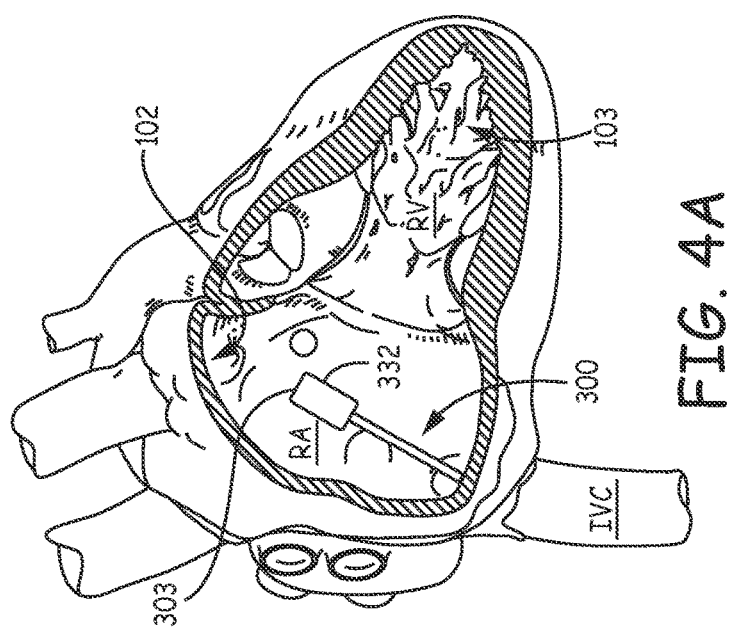
FIG. 4A
FIG. 4B
FIG. 4C

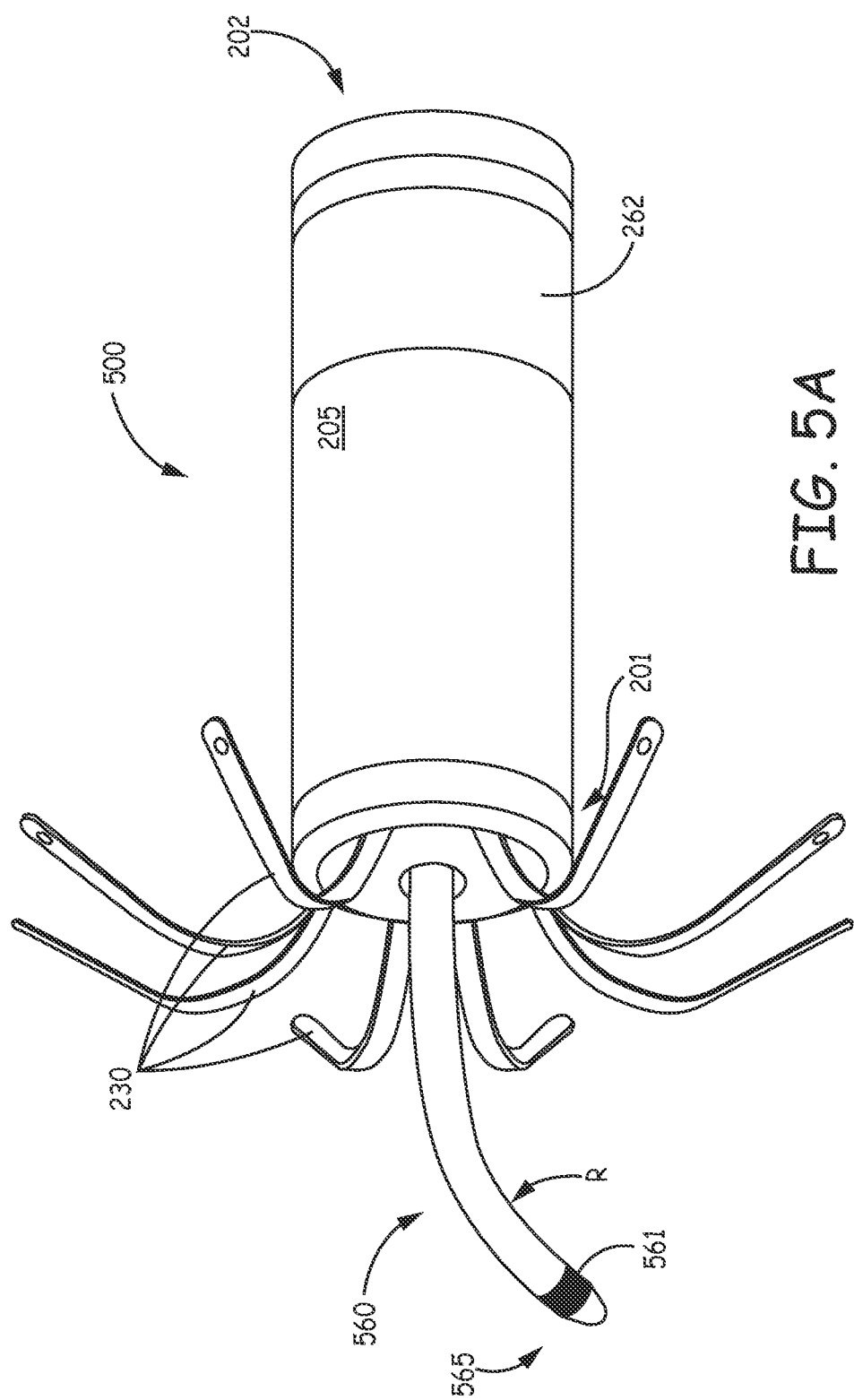

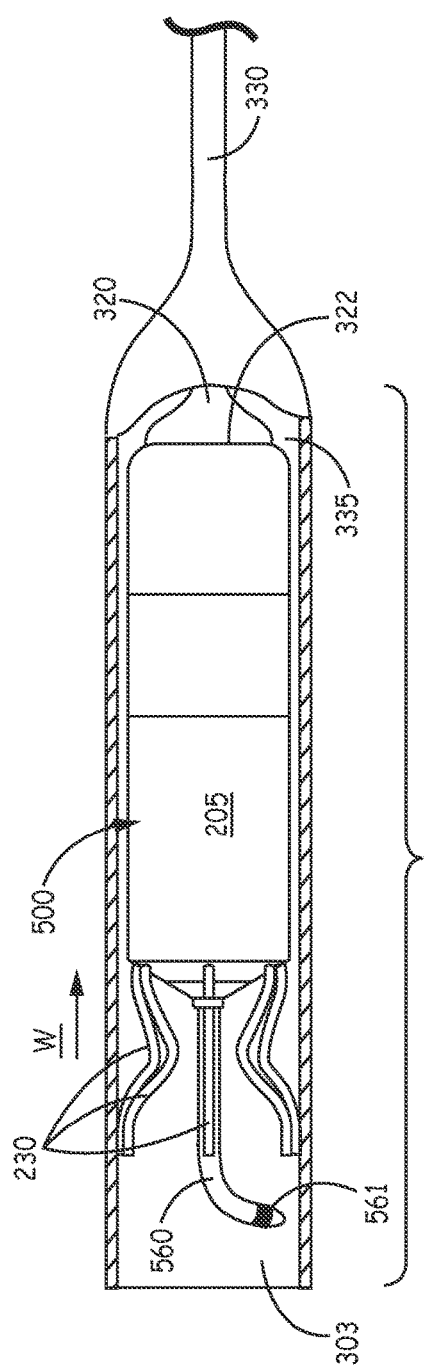
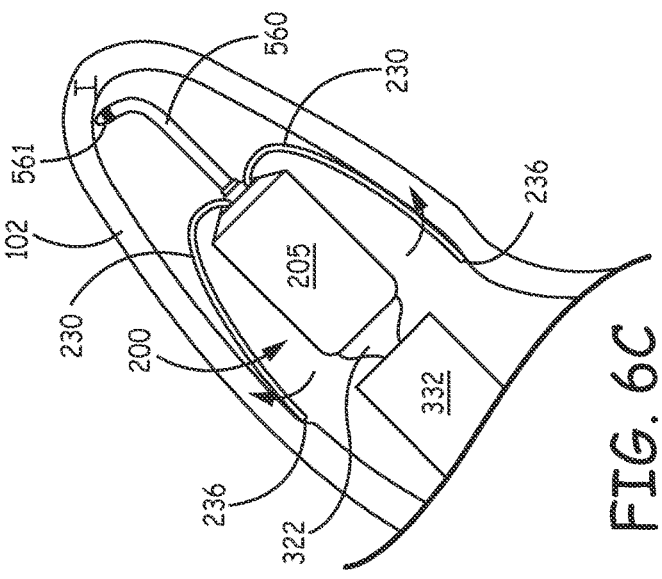
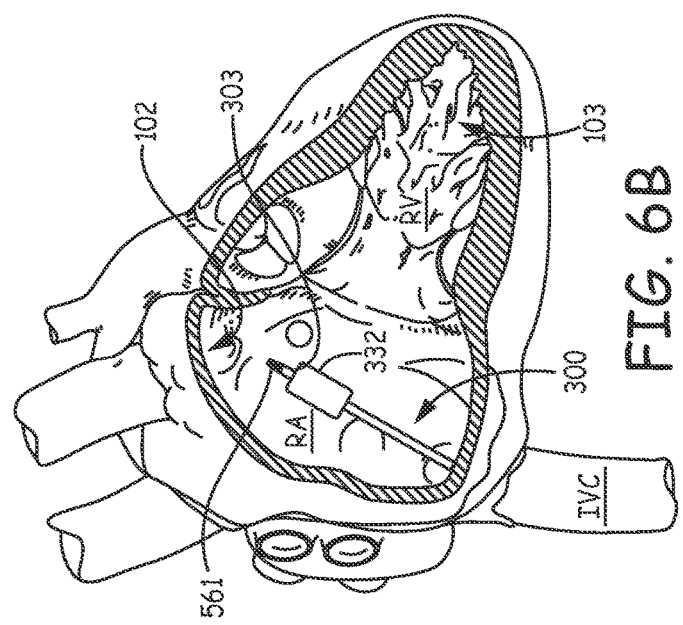
FIG. 6A
FIG. 6B
FIG. 6C

INTERVENTIONAL MEDICAL DEVICE AND METHOD OF USE

CROSS-REFERENCE TO RELATED APPLICATION

The present application is a continuation of U.S. patent application having the Ser. No. 16/686,617, which was filed on Nov. 18, 2019, which is a continuation of U.S. patent application having the Ser. No. 14/518,261, which was filed on Oct. 20, 2014, and claims the benefit of U.S. Provisional Patent Application having the Ser. No. 62/041,954, which was filed on Aug. 26, 2014. Application Ser. Nos. 16/686,617, 14/518,261 and 62/041,954 are hereby incorporated by reference in their entirety. The present application is related to commonly assigned U.S. patent application Ser. No. 14/518,211, which was filed on Oct. 20, 2014 and entitled INTERVENTIONAL MEDICAL SYSTEMS, DEVICES, AND COMPONENTS THEREOF, and which is incorporated by reference in its entirety.

FIELD OF THE DISCLOSURE

The present disclosure pertains to interventional medical systems, and more particularly to relatively compact implantable medical devices thereof and associated methods.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. An implanting physician may employ a standard guiding catheter (not shown) to deliver a relatively compact medical device to any one of the three exemplary sites, for example, according to methods known in the art of interventional cardiology, by maneuvering the catheter, with the device loaded therein, up through the inferior vena cava IVC and into the right atrium RA. However, a co-pending and commonly assigned U.S. patent application having the Ser. No. 14/039,937 discloses a more sophisticated delivery tool, which the operator may employ, in lieu of the standard guiding catheter, to deliver and to fix the device at the desired implant site.

SUMMARY

A relatively compact implantable medical device, according to embodiments of interventional medical systems disclosed herein, includes a fixation member formed by a plurality of fingers mounted around a perimeter of a distal end of a housing of the device; each finger is elastically deformable from a relaxed condition to an extended condition, to accommodate delivery of the device to a target implant site, and from the relaxed condition to a compressed condition, to accommodate wedging of the fingers between opposing tissue surfaces at the target implant site, wherein the compressed fingers hold a cardiac pacing electrode of the device in intimate tissue contact for the delivery of pacing stimulation from the implanted device to the site. According to some methods, after an operator navigates a delivery tool, which has the device loaded within a distal-most portion of a deployment tube thereof, through a venous system of the patient, to locate the distal-most portion of the tool in proximity to a target implant site, the operator retracts the deployment tube with respect to the loaded device to expose the fixation fingers out through a distal opening of the lumen of the deployment tube, so that the fixation fingers are released from the extended condition to the relaxed condition; and then the operator advances the delivery tool toward the target site to wedge the exposed fixation fingers between opposing tissue surfaces at the target implant site, thereby compressing the fixation fingers, so that the compressed fingers, by a spring force thereof, hold the pacing electrode of the device in intimate tissue contact.

Each finger of the device fixation member, according to some embodiments, includes a first segment, which extends from a fixed end of the corresponding finger, and a second segment that extends from the first segment to a free end of the corresponding finger, wherein each second segment extends in a distal direction, when the first segment of each finger is in the extended condition, and extends in a proximal direction, outward from the device housing, when the first segment of each finger is in the relaxed condition. Furthermore, the second segment of each fixation finger is preferably configured to prevent penetration thereof within the tissue when the fingers are compressed and wedged between opposing tissue surfaces.

According to some preferred embodiments, the pacing electrode of the device is mounted on a pacing extension of the device, wherein the pacing extension extends distally from the distal end of the device housing. When the device is loaded in the distal-most portion of the aforementioned delivery tool, an entirety of the pacing extension may be contained within the distal-most portion, along with a remainder of the device and the distal end of the inner member of the tool, which abuts a proximal end of the device housing, and each fixation finger, in the extended condition, extends in a distal direction alongside the pacing extension. According to some embodiments and methods, after navigating the delivery tool to locate the distal-most portion of the tool in proximity to the target implant site, the operator can retract the deployment tube only enough to expose the pacing electrode of the pacing extension without exposing the fixation fingers, and then advance the delivery tool toward the target site until the exposed electrode comes into contact with tissue at the site, so that the operator can evaluate pacing performance at the site. If pacing performance is acceptable at the site, the operator can pull the tool and loaded device back away from the site, retract the deployment tube even further, with respect to the loaded device, to expose the fixation fingers, and then advance the tool again toward the site to wedge the exposed fixation fingers between opposing tissue surfaces at the target implant site, thereby compressing the fixation fingers, so that the compressed fingers hold the pacing electrode in intimate tissue contact.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a perspective view of an implantable medical device, according to some embodiments;

FIGS. 4A-C are schematics outlining some methods of the present invention;

FIG. 5A is a perspective view of an implantable medical device, according to some additional embodiments;

FIGS. 6A-C are schematics according to some alternate methods of the present invention.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
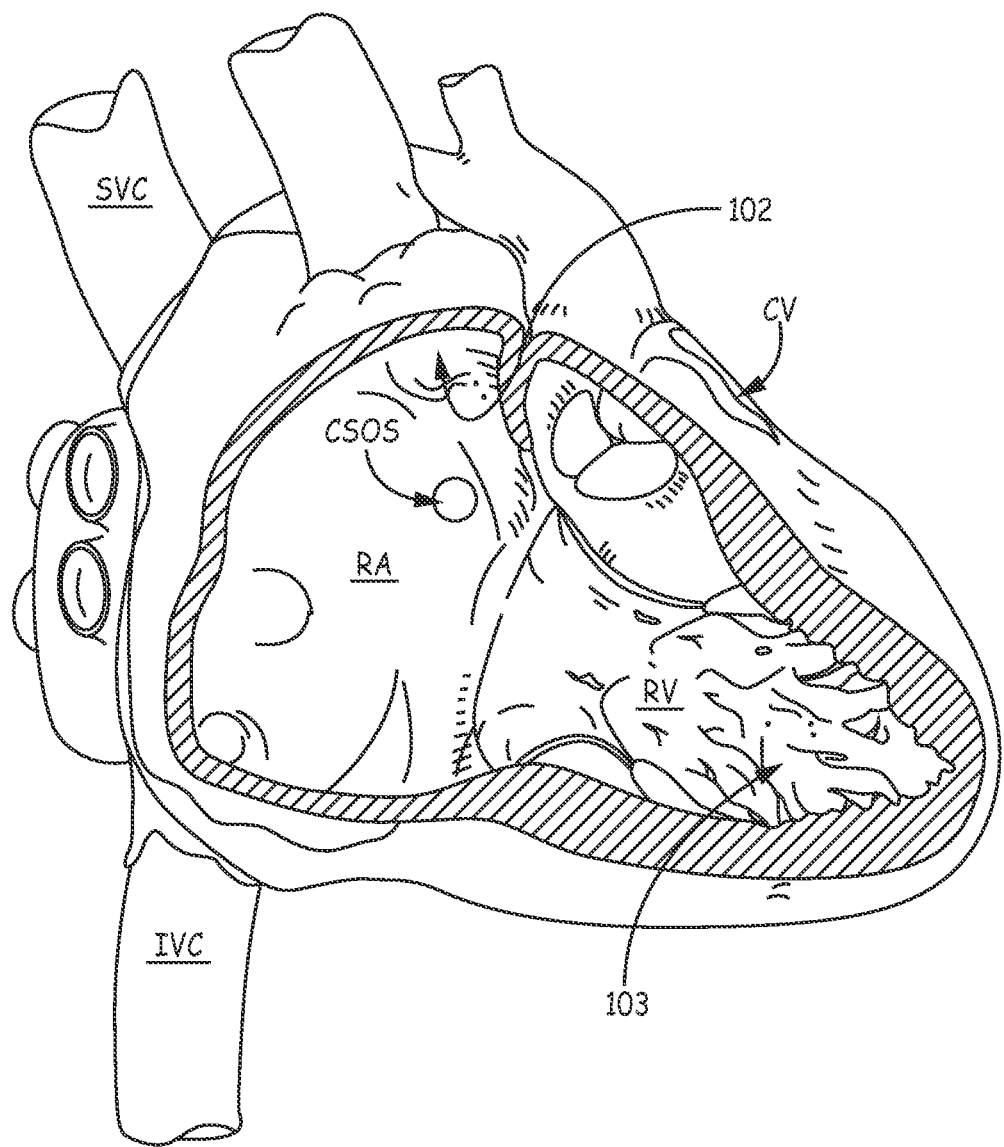
FIG. 1 is a schematic diagram showing potential implant sites for embodiments of the present invention.

FIG. 2A is a perspective view of an implantable medical device 200, according to some embodiments. FIG. 2A illustrates device 200 including a hermetically sealed housing 205, preferably formed from a biocompatible and biostable metal such as titanium, which contains a pulse generator (e.g., a power source and an electronic controller—not shown), a fixation member, which is formed by a plurality of fixation fingers 230 spaced apart from one another around a perimeter of a distal end 201 of housing 205, and an electrode 261, which is located at the distal end 201 of housing 205 being coupled to the controller of device 200 by a hermetic feedthrough assembly (not shown) constructed according to those known to those skilled in the art of implantable medical devices. Housing 205 may be overlaid with an insulative layer, for example, medical grade polyurethane, parylene, or silicone, and FIG. 2A further illustrates another electrode 262 of device 200, which may be formed by removing a portion of the insulative layer to expose the metallic surface of housing 205. According to the illustrated embodiment, electrode 262 may function in conjunction with electrode 261 for bipolar pacing and sensing, when fixation fingers 230 hold electrode 261 in intimate tissue contact at a target implant site, for example, within right atrial appendage 102 or within right ventricle RV in proximity to apex 103 (FIG. 1). Fixation fingers 230 function to hold device 200 at the implant site by being wedged between opposing tissue surfaces at the site.

Figure 2C:
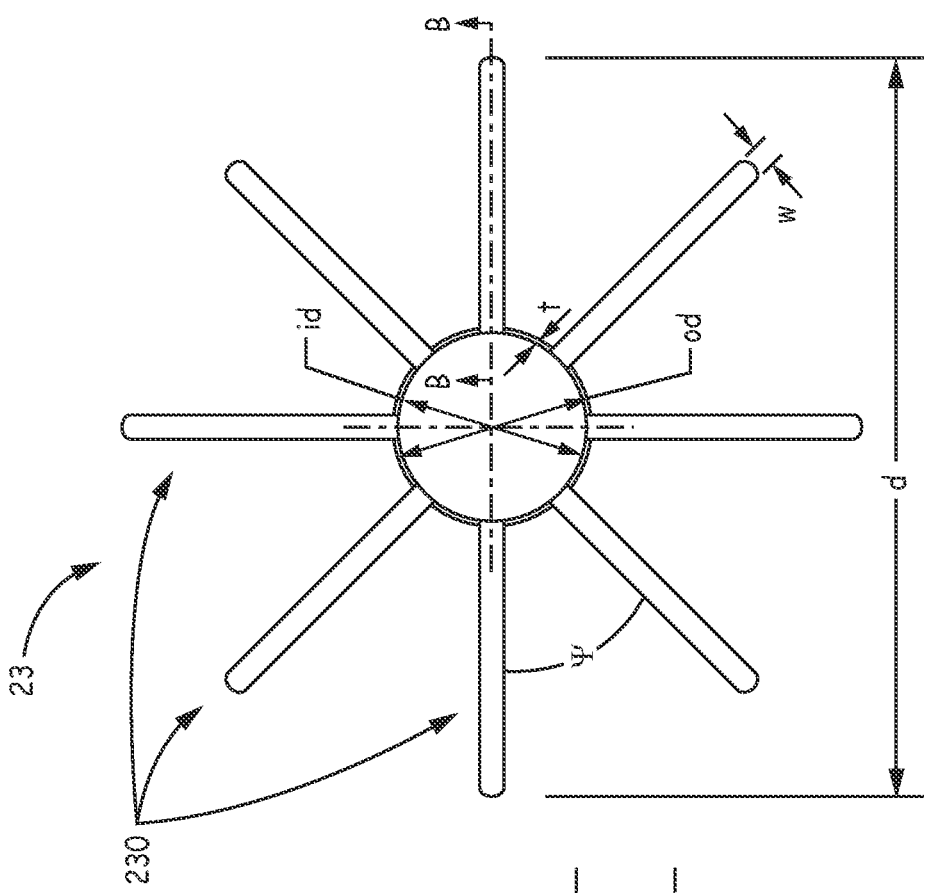
FIGS. 2B-C are elevation and end views of a fixation member component which may be employed by the device of FIG. 2, according to some embodiments.
Figure 2B:
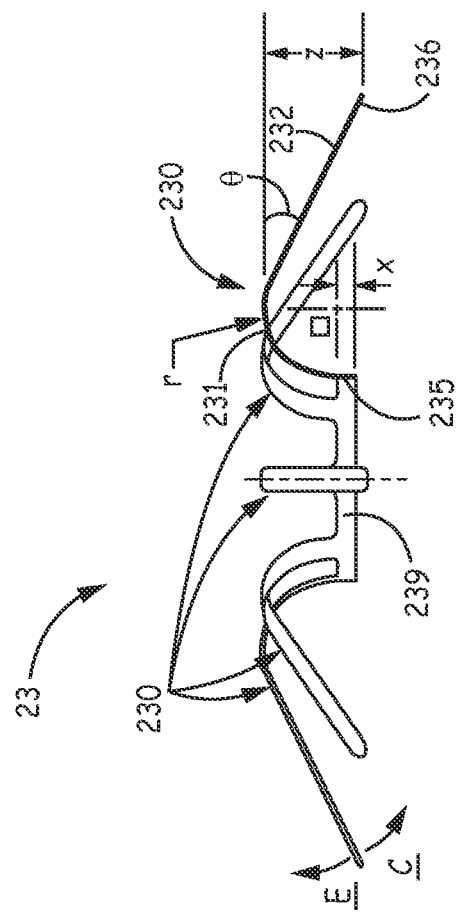

FIGS. 2B-C are elevation and end views of an exemplary fixation member component 23 which may be employed by device 200, according to some embodiments. FIGS. 2B-C illustrate fixation member component 23 including eight fixation fingers 203 integrally formed with one another and a base ring 239, such that a thickness t of base ring 239 is approximately the same as that of each finger 230. According to an exemplary embodiment, fixation member component 23 is cut from Nitinol tubing, according to methods known in the art, and thickness t may be 0.005 inch+/−0.001 inch, wherein base ring 239 may have an inner diameter id of approximately 0.20 inch and an outer diameter od of approximately 0.21 inch. A height x of base ring 239 may be approximately equal to a width w of each finger, for example, approximately 0.024 inch. After cutting the aforementioned Nitinol tubing, fingers 230 are shaped by bending and holding fingers 230 in the illustrated curvature while heat treating component 23 according to methods known to those skilled in the art. FIG. 2B illustrates (via cross-section through section line B-B of FIG. 2C) each fixation finger 230 including a first segment 231 and a second segment 232, wherein each first segment 231 extends from a fixed end 235 of the corresponding finger 230 to the corresponding second segment 232, and each second segment 232 extends from the corresponding first segment 231 to a free end 236 of the corresponding finger 230. FIGS. 2A-B further illustrates each first segment 231, in a relaxed condition, extending in an arc, distally and outwardly from fixed end 235, and second segment 232 extending from first segment 231 in a proximal direction and outward from device housing 205. With further reference to FIG. 2C fixation fingers 230 are spaced equally apart from one another such that an angle Ψ defined between each adjacent pair is approximately 45 degrees. Component 23 may be mounted to distal end 201 of device housing 205, for example, in a manner similar to that described for a fixation component 102 in co-pending and commonly assigned United States Patent Application 2012/0172690, which description is hereby incorporated by reference.

Figure 3:
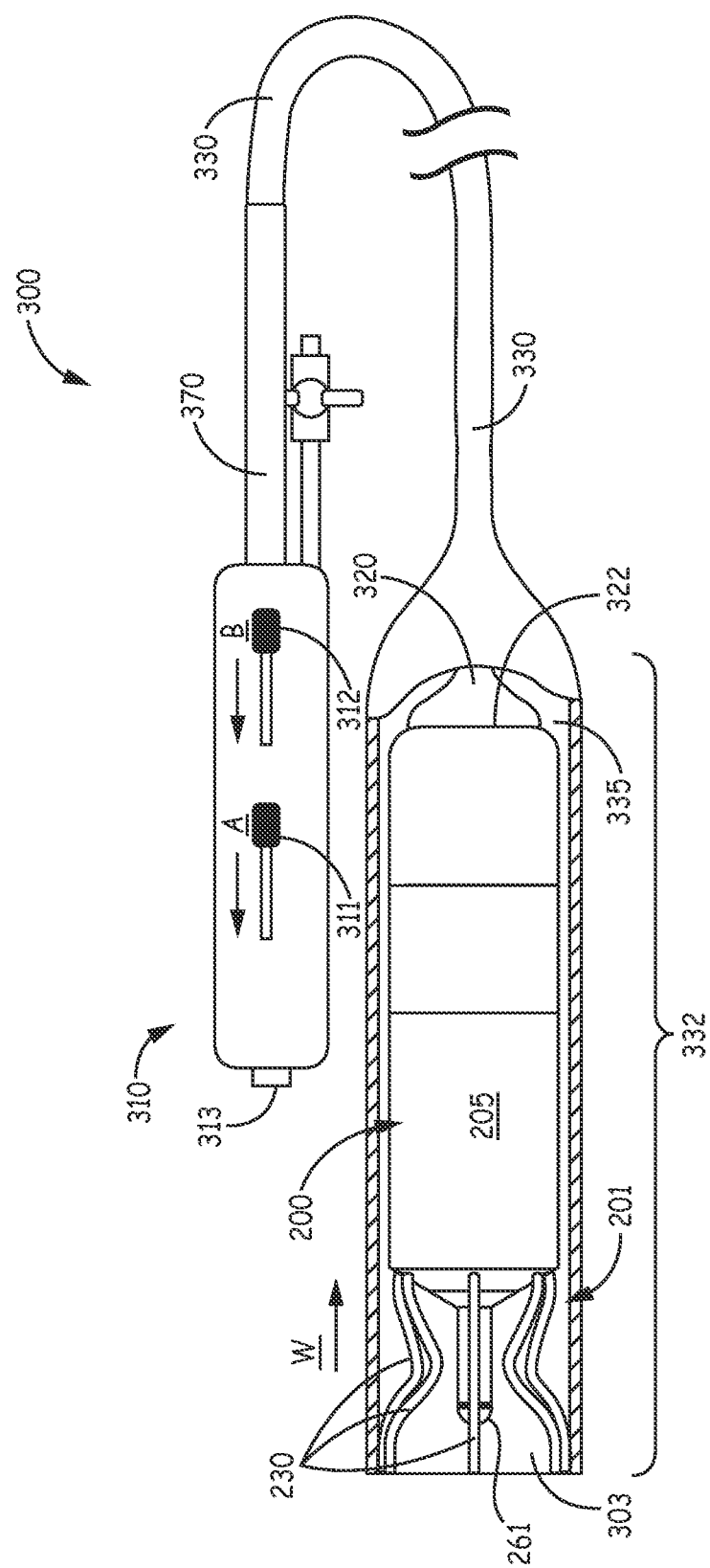
FIG. 3 is a plan view of an interventional medical system with a partial cut-away section, according to some embodiments.

According to the illustrated embodiment, first segment 231 of each fixation finger 230 is elastically deformable between the relaxed condition and an extended condition, per arrow E of FIG. 2B, and between the relaxed condition and a compressed condition, per arrow C of FIG. 2B. The extended condition is described below in conjunction with FIGS. 3, 4A, and 6A-B; and the compressed condition is described below in conjunction with FIGS. 4C and 6C. With further reference to FIG. 2B, the angle enclosed by the arc of first segment 231 of each finger 230 is shown being at least 90 degrees, with second segment 232 extending away from first segment 231 at an angle θ. According to an exemplary embodiment, a radius r of the arc of each first segment 231 is approximately 0.067 inch, and angle θ is approximately 26 degrees. FIG. 2B further illustrates each second segment 232 extending in a proximal direction from first segment 231 over a distance just slightly greater than a distance z, wherein distance z may be approximately 0.095 inch measured from a proximal edge of base ring 239 to a tangent line extending from an intersection of first and second segments 231, 232. Although not shown in FIG. 2A, according to some preferred embodiment, electrode 261 may be mounted on a relatively short extension formed in distal end 201 of housing 205 such that electrode 261 is spaced distal to radius r of each finger 230, for example, as shown in FIGS. 3 and 4B, wherein the distance from the apex of radius r to the distally spaced electrode 261 may be approximately 2 mm. Furthermore, it should be noted that if the exemplary dimensions of component 23, presented in conjunction with FIGS. 2B-C, are scaled down, for example, in proportion to a smaller overall implantable device volume, they will still fall within the scope of embodiments of the present invention.

FIG. 3 is a plan view of an interventional medical system with a partial cut-away section, according to some embodiments, wherein the system includes a delivery tool 300, in which device 200 is loaded, for deploying device 200 to a target implant site. FIG. 3 illustrates tool 300 including a handle 310, an elongate inner member 320, and an outer assembly, which is formed by an elongate deployment tube 330 and an outer, stabilizing sheath 370 that is secured to handle 310 and surrounds a proximal portion of deployment tube 330 in proximity to handle 310. According to the illustrated embodiment, elongate inner member 320 extends within a lumen 335 of deployment tube 330, and a proximal end of deployment tube 330 is coupled to a control member 312 of handle 310 such that an entirety of deployment tube 330 is movable with respect to the inner member 320, via control member 312. FIG. 3 further illustrates inner member 320 including a distal end 322, which is located within a distal-most portion 332 of deployment tube 330, and which is configured to engage implantable medical device 200 by abutting proximal end 202 of device housing 205, as shown.

With further reference to FIG. 3, that portion of deployment tube lumen 335 which extends along a length of distal-most portion 332 is sized to contain distal end 322 of inner member 320 together with an entirety of device 200. FIG. 3 shows fixation fingers 230 of the loaded device 200 being held by distal-most portion 332 in the aforementioned extended position. With reference to FIG. 4A, a distal portion of tool 300, with an entirety of device 200 loaded in distal-most portion 332, may be navigated to a target implant site, for example, in the right atrium RA (or right ventricle RV), by advancing tool 300 through a venous system of the patient, for example, from a femoral venous access site and up through the inferior vena cava IVC. A length of deployment tube 330, between handle 310 and a distal opening 303 of deployment tube 330, when tube 330 is in the position shown in FIG. 3, may be between approximately 103 cm and approximately 107 cm, for example, to reach the right atrium RA from the femoral access site. According to some embodiments of the present invention, delivery tool 300 includes articulating features to facilitate the navigation of the distal portion of delivery tool 300; for example, inner member 320 of delivery tool 300 may include a pull wire (not shown) integrated therein and coupled to another control member 311 of handle 310 that, when moved per arrow A, causes inner member 320 and deployment tube 330 to bend along distal portions thereof. Suitable construction detail for a delivery tool like tool 300 is described in co-pending and commonly assigned U.S. patent application, Ser. No. 14/039,937, the description of which is hereby incorporated by reference.

According to some methods of the present invention, once an operator has located distal-most portion 332 in a chamber of the heart, for example, the right atrium RA, as shown in FIG. 4A, the operator can retract deployment tube 330, per arrow W (FIG. 3), for example, by moving control member 312 per arrow B (FIG. 3), to release fixation fingers 230 to the relaxed position as shown in FIG. 4B. FIG. 4B illustrates each finger 230 having been exposed out through distal opening 303 of deployment tube 330 so that, in the relaxed position, each finger 230 extends in a proximal direction and outward from device housing 205. Then, after releasing device fixation fingers 230, the operator may advance tool 300 and device 200 together to a target implant site between folds of tissue, for example, pectinate muscle bands in right atrial appendage 102, and, thus, wedge the exposed fixation fingers 230 between opposing tissue surfaces as shown schematically in FIG. 4C. With reference to FIG. 4C, distal end 322 of device inner member 320 may be employed to provide a push force that assists in wedging fingers 230 so that fingers 230 are in the aforementioned compressed state to hold electrode 261 in intimate tissue contact. With reference back to FIG. 2, according to some embodiments, one or more of finger free ends 236 includes a discrete radiopaque marker 238 attached thereto, for example, a platinum-iridium rivet like member. Optional marker(s) 238 may assist the operator in assessing the fixation of device 200 at the implant site. It should be noted that the compressed fingers 230, having a super-elastic nature, hold device 200 in place at the implant site by a spring force (per the bold arrows of FIG. 4C), and that finger free ends 236 are preferably configured to prevent penetration thereof within tissue at the implant site, while merely catching, or lodging against opposing tissue surfaces. Furthermore, with reference to FIG. 4A, an alternate implant site may be in the right ventricle RV, where fixation fingers 230 may be wedged between folds of tissue (trabeculae) in the area of apex 103. It should be noted that the fixation fingers 230, as described above in conjunction with FIGS. 2B-C, may also be formed from a polymer material, either individually or integrally with base ring 239, wherein an appropriate polymer material and associated dimensional specifications essentially mimics that of fingers 230 formed from the aforementioned Nitinol, in terms of spring properties.

After wedging fingers 230 between opposing tissue surface, the operator may evaluate pacing performance of electrode 261 before completely withdrawing delivery tool 300 away from the implanted device 200. Thus, if the operator determines that the performance is not satisfactory, the operator may advance distal-most portion 332 of deployment tube 330 back in a distal direction, for example, via control member 312 (FIG. 3), relative to device 200 and inner member 320 and over wedged fixation fingers 230 to move device 200 back into distal-most portion 332 with fingers 230 moved back into the extended condition, as shown in FIG. 3. Then the operator can move delivery tool 300 with the re-loaded device 200 into proximity with an alternative implant site, retract deployment tube 330 again to expose and release fingers 230 into the relaxed condition (FIG. 4B), and then advance tool 300 toward the other site to wedge the exposed fingers 230 between opposing tissue surfaces at the other site (FIG. 4C).

Figure 5B:
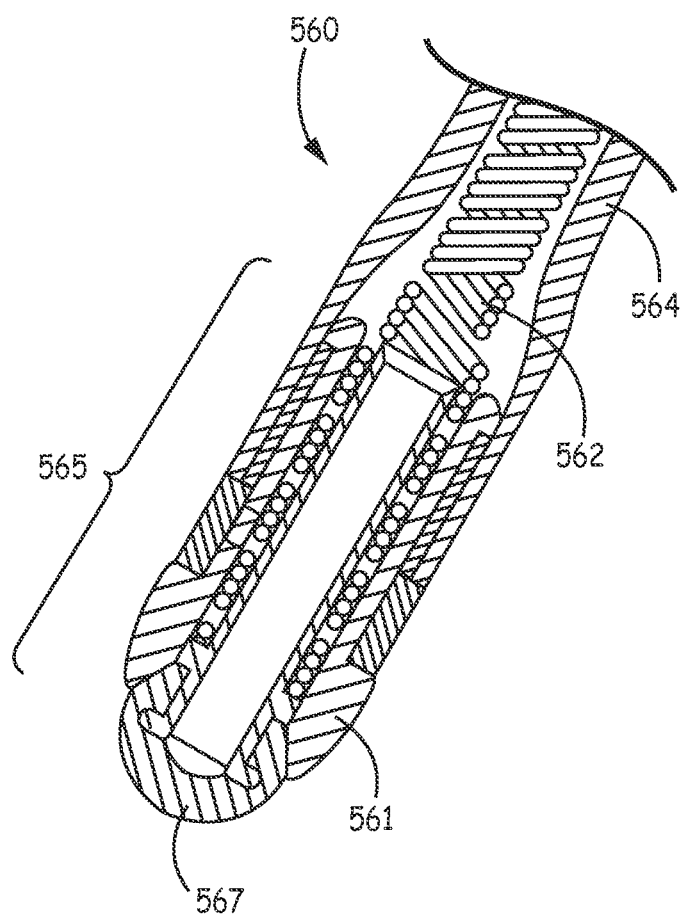
FIG. 5B is a cross-section view through a portion of the device of FIG. 5A, according to an exemplary construction of some embodiments.

FIG. 5A is a perspective view of an implantable medical device 500, according to some additional embodiments; and FIG. 5B is a cross-section view through a portion of device 500, according to an exemplary construction of some embodiments. FIG. 5A illustrates device 500 being similar to device 200 but including a pacing extension 560 on which a pacing electrode 561 is mounted, in lieu of electrode 261 of device 200. FIG. 5A further illustrates extension 560 including a preformed curvature located in proximity to, and proximal to electrode 561. A diameter of extension 560 may be approximately 0.05 inch (1.3 mm); an overall length of extension 560 may be approximately 0.6 inch (15 mm); and the curvature, preferably in a single plane, is defined by a radius R, which may be approximately 0.2 inch, according to an exemplary embodiment. According to the illustrated embodiment, electrode 561 is located in close proximity to a distal tip 565 of extension 560, which tip 565 is preferably tapered. FIG. 5B illustrates distal tip 565 being slightly enlarged from a remainder of extension 560; and, according to some embodiments, tip 565 includes electrode 561, which forms at least a portion of the taper, and a relatively soft medical grade silicone rubber member 567, which may include a steroid embedded therein. The illustrated contour of electrode 561 may help electrode 561 to make better tissue contact when tip 565 lies adjacent to tissue, for example, as illustrated in FIG. 6C. According to an exemplary embodiment, a diameter of tip 565 (as shown in FIG. 5B) is approximately 0.07 inch (1.8 mm), and a surface area of electrode 561 is approximately 5.8 mm$^2$. Electrode 561 may be formed from a platinum iridium alloy.

FIG. 5B further illustrates pacing extension 560 being formed by a coiled multi-filar conductor 562 (e.g., MP35N alloy) enclosed within a jacket of insulation 564 (e.g., medical grade polyurethane), and an exemplary junction between electrode 561 and conductor 562, which may be secured by crimping and/or welding according to methods known in the art of implantable medical electrical leads. According to the illustrated embodiment, conductor 562 electrically connects electrode 561 to the aforementioned pulse generator contained within device housing 205, for example, via a feedthrough assembly constructed according to methods known in the art of implantable medical devices.

Turning now to FIG. 6A, as was described above for device 200, device 500 is loaded into distal-most portion 332 of delivery tool 300 (FIG. 3), such that fixation fingers 230 are in the extended condition. FIG. 6A illustrates fingers 230 extending in a distal direction and alongside pacing extension 560 within distal-most portion 332. After device 500 is loaded, the operator may navigate delivery tool 300, with device 500 completely contained therein, through the patient's venous system, for example, from a femoral venous access site, up through the inferior vena cava IVC, and into a chamber of the heart, for example, the right atrium RA, as shown in FIG. 4A. In some preferred embodiments, pacing extension 560 extends distally beyond extended fingers 230 so that the operator may withdraw deployment tube 330, per arrow W, just enough to expose electrode 561 out through distal opening 303 thereof, as shown in FIG. 6B. According to some exemplary embodiments, extension 560 can extend approximately 2 to 4 mm beyond opening 303 without fingers 230 being exposed, so that the operator can advance tool 300 to one or more potential implant sites, where electrode 561 makes contact, to map electrical activity and/or to check pacing thresholds. According to some methods, after finding a desired implant site in this manner, the operator can pull back tool 300 and device 500 together, for example, to the position shown in FIG. 6B, and then retract deployment tube 330 even further, with respect to device 500 and inner member 320, to expose fixation fingers 230 out from distal opening 303, thereby releasing fingers 230 to the relaxed condition (FIG. 4B). Then, as described above, the operator can advance tool 300 and device 500 together back to the desired implant site, for example, between pectinate muscle bands in right atrial appendage 102, and, thus, wedge the exposed fixation fingers 230 between opposing tissue surfaces as shown schematically in FIG. 6C, to hold device 500 at the implant site with electrode 561 making intimate tissue contact. With further reference to FIG. 6C, it may be appreciated that the length of pacing extension 560 serves to separate that portion of the implant site at which electrode 561 makes contact with that portion of the site at which fixation fingers 230 make spring contact (e.g., per bold arrows), so that any inflammation associated with the fixation fingers contact may not impair chronic pacing thresholds.

Figure 7:
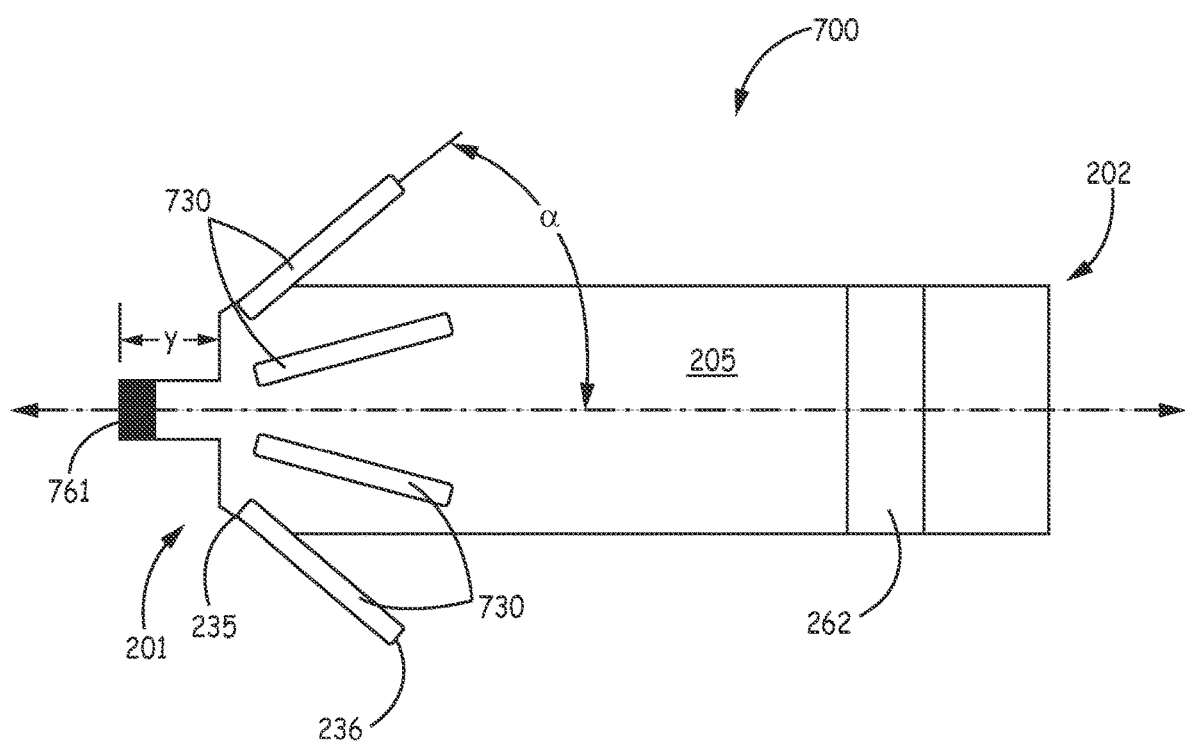
FIG. 7 is a perspective view of an implantable medical device, according to some alternate embodiments.

FIG. 7 is a plan view of an implantable medical device 700, according to some alternate embodiments. FIG. 7 illustrates device 700 being similar to device 200 of FIG. 2, in that device 700 includes hermetically sealed housing 205, which may be overlaid with an insulative layer, for example, medical grade polyurethane, parylene, or silicone, and wherein electrode 262 may be formed by removing a portion of the insulative layer to expose the metallic surface of housing 205. FIG. 7 further illustrates device 700 including a fixation member, which is formed by a plurality of fixation fingers 730, for example, eight fingers, spaced apart from one another around a perimeter of a distal end 201 of housing 205, and an electrode 761, which is spaced distally apart from distal end 201 of housing 205 by a distance y, which may be approximately 2 mm, for example, to allow electrode 761 to make better tissue contact along uneven surfaces such as between pockets created by relatively small pectinate muscle bands in right atrial appendage 102 (FIG. 1). With reference back to FIG. 2A, it should be noted that electrode 261 of device 200 may be similarly spaced from distal end 201 of housing 205. Electrode 761, like electrode 261, may be coupled to the controller of device 200 by a hermetic feedthrough assembly to function in conjunction with electrode 262 for bipolar pacing and sensing.

According to the illustrated embodiment, fixation fingers 730 are formed from a flexible polymer material, for example, medical grade silicone rubber or polyurethane, and, in a relaxed condition, extend proximally from distal end 201 of device housing 205, and outward therefrom at an angle α relative to a longitudinal axis of device housing 205. Angle α may be approximately 60 degrees, and a length of each finger 730, from a fixed end 735 to a free end 736 thereof, may be approximately 0.2 inch (5 mm). Like the above described fixation fingers 230, fingers 730 are configured to hold electrode 761 in intimate tissue contact at a target implant site, for example, within right atrial appendage 102 or within right ventricle RV in proximity to apex 103 (FIG. 1), but, being relatively softer than Nitinol, silicone rubber or polyurethane fingers may be less likely to migrate through tissue at the implant site over time.

In the foregoing detailed description, the invention has been described with reference to specific embodiments. However, it may be appreciated that various modifications and changes can be made without departing from the scope of the invention as set forth in the appended claims.

We claim:

1. A method for deploying an implantable medical device to a target implant site located in a chamber of a patient's heart, the device comprising a hermetically sealed housing containing an electronic controller and a pacing electrode electrically coupled to the controller and mounted in proximity to a distal end of the housing, the device comprising a fixation member located at the distal end of the housing, the device positioned in a distal-most portion of a deployment tube of a delivery tool wherein a proximal end of the device abuts a distal end of an inner member of the delivery tool, the method comprising:

navigating the delivery tool with the device positioned in the distal-most portion of the deployment tube through a venous system of the patient to locate the distal-most portion of the deployment tube in the chamber of the heart;

retracting the deployment tube of the delivery tool with respect to the inner member of the tool and the device, thereby exposing the pacing electrode;

advancing the delivery tool toward the target implant site to bring the exposed pacing electrode into contact with tissue at the target implant site; and evaluating, prior to penetrating the tissue with the fixation member, performance of the pacing electrode when in contact with the tissue.

2. The method of claim 1, wherein navigating the delivery tool comprises advancing the delivery tool from a femoral venous access site.

3. The method of claim 1, wherein navigating the delivery tool comprises advancing the delivery tool through an inferior vena cava.

4. The method of claim 1, wherein the chamber of the heart is the right atrium.

5. The method of claim 1, wherein the chamber of the heart is the right ventricle.

6. The method of claim 1, further comprising determining, based on the performance of the pacing electrode, whether the pacing electrode is in contact with a desired implant site.

7. The method of claim 6, further comprising fixating the device to the tissue if the device is found to be in contact with the desired implant site.

8. The method of claim 1, wherein evaluating the performance of the pacing electrode comprises mapping electrical activity of the heart.

9. The method of claim 1, wherein evaluating the performance of the pacing electrode comprises checking a pacing threshold.

10. The method of claim 1, further comprising fixating the device to the tissue using the fixation member.

11. The method of claim 10, wherein the fixation member comprises a plurality of fixation fingers.

12. The method of claim 10, wherein the fixation member comprises a plurality of projections having a flat cross section with a greater width than thickness.

13. The method of claim 1, wherein the pacing electrode is coupled to the electronic controller via a feedthrough assembly.

14. The method of claim 1, wherein the delivery tool further comprises a handle secured to a proximal end of the deployment tube, and the handle comprises a control member which is operable to facilitate retraction of the deployment tube relative to the inner member.

15. The method of claim 1, wherein the deployment tube comprises a distal opening that terminates the distal end of the deployment tube.

16. The method of claim 1, wherein the distal-most portion of the deployment tube is larger in diameter than an adjacent proximal portion of the deployment tube.

17. The method of claim 16, wherein the distal-most portion of the deployment tube is configured to contain the medical device and a distal end of the inner member of the tool.

18. The method of claim 17, wherein the distal-most portion of the deployment tube is further configured to contain the fixation member in a location within the distal-most portion of the deployment tube, distal of the device housing.

19. The method of claim 1, wherein a length of the deployment tube is between approximately 103 cm and approximately 107 cm.

20. The method of claim 1, further comprising:
retracting the deployment tube to expose the fixation member out from a distal opening defined by the deployment tube; and evaluating performance of the pacing electrode after exposing the fixation member out through the distal opening and prior to fixating the device to the tissue.

21. The method of claim 1, further comprising:
displacing, after evaluating the performance of the pacing electrode and prior to fixating the device to the tissue, the delivery tool away from the target implant site and moving the delivery tool into proximity with a second target implant site within the chamber of the heart;

evaluating, prior to fixating the device to tissue at the second target implant site, performance of the pacing electrode when in contact with the tissue at the second target implant site, fixating the device to the tissue at the second implant site if the device is found to be in contact with the second implant site.

22. A method for deploying an implantable medical device to a target implant site located in a chamber of a patient's heart, the medical device comprising a hermetically sealed housing containing an electronic controller and a pacing electrode electrically coupled to the controller and mounted in proximity to a distal end of the housing, and the medical device comprising a fixation member located in proximity to the distal end of the housing, the method comprising:

loading the medical device into a distal-most portion of a deployment tube of a delivery tool such that a distal end of an inner member of the delivery tool engages a proximal end of the medical device;

advancing the delivery tool with the medical device positioned in the distal-most portion of the deployment tube through a venous system of the patient to locate the distal-most portion of the tube in the chamber of the heart;

retracting the deployment tube of the delivery tool with respect to the inner member of the delivery tool and the medical device;

advancing the delivery tool toward the target implant site to bring the pacing electrode into contact with tissue at the target implant site; and evaluating, prior to penetrating the tissue with the fixation member, performance of the pacing electrode when in contact with the tissue.

23. The method of claim 22, further comprising determining, based on the performance of the pacing electrode, whether the pacing electrode is in contact with a desired implant site.

24. The method of claim 23, further comprising fixating the device to the tissue if the medical device is found to be in contact with the desired implant site.

25. The method of claim 22, further comprising fixating the device to the tissue using the fixation member.

26. The method of claim 22, wherein the delivery tool further comprises a handle secured to a proximal end of the deployment tube, and the handle comprises a control member which is operable to facilitate retraction of the deployment tube relative to the inner member.

27. The method of claim 22, wherein the distal-most portion of the deployment tube is larger in diameter than an adjacent proximal portion of the deployment tube.

28. The method of claim 27, wherein the distal-most portion of the deployment tube is configured to contain the medical device and a distal end of the inner member of the tool.

29. The method of claim 28, wherein the distal-most portion of the deployment tube is further configured to contain the fixation member in a location within the distal-most portion of the deployment tube, distal of the device housing.

\* \* \* \* \*